United States Patent
Kuhle

(10) Patent No.: US 6,482,169 B1
(45) Date of Patent: Nov. 19, 2002

(54) DOUBLE-LUMEN CATHETER

(75) Inventor: William G. Kuhle, 655 Goodpasture Island Rd., Apt. 170, Eugene, OR (US) 97401-1533

(73) Assignee: William G. Kuhle, Eugene, OR (US)

( * ) Notice: Subject to any disclaimer, the term of this patent is extended or adjusted under 35 U.S.C. 154(b) by 7 days.

(21) Appl. No.: 09/877,827

(22) Filed: Jun. 8, 2001

Related U.S. Application Data

(60) Provisional application No. 60/210,294, filed on Jun. 8, 2000.

(51) Int. Cl.$^7$ ............................................. A61M 37/00
(52) U.S. Cl. ..................................... 604/6.16; 607/105
(58) Field of Search .................... 604/6.16, 43, 524, 604/103.13, 508; 600/562; 607/105

(56) References Cited

U.S. PATENT DOCUMENTS

| | | | | |
|---|---|---|---|---|
| 4,770,652 A | * | 9/1988 | Mahurkar | 604/6.16 |
| 5,163,928 A | | 11/1992 | Hobbs et al. | |
| 5,171,216 A | * | 12/1992 | Dasse et al. | 604/43 |
| 5,209,723 A | | 5/1993 | Twardowski et al. | |
| 5,222,949 A | * | 6/1993 | Kaldany | 604/524 |
| 5,405,320 A | | 4/1995 | Twardowski et al. | |
| 5,486,159 A | * | 1/1996 | Mahurkar | 604/6.16 |
| 5,509,897 A | | 4/1996 | Twardowski et al. | |
| 5,569,195 A | * | 10/1996 | Saab | 604/103.13 |
| 5,718,692 A | * | 2/1998 | Schon et al. | 604/264 |
| 5,947,953 A | | 9/1999 | Ash et al. | |
| 6,001,079 A | | 12/1999 | Pourchez | |
| 6,413,228 B1 | * | 7/2002 | Hung et al. | 600/562 |
| 2002/0013569 A1 | * | 1/2002 | Sterman et al. | 604/508 |
| 2002/0091430 A1 | * | 7/2002 | Dobak, III et al. | 607/105 |

* cited by examiner

*Primary Examiner*—Teresa Walberg
*Assistant Examiner*—Leonid M Fastovsky
(74) *Attorney, Agent, or Firm*—Morrison & Foerster LLP

(57) ABSTRACT

A catheter is described. In one embodiment, the catheter includes: a shaft segment including a shaft segment uptake lumen and a shaft segment return lumen; and a distal end segment coupled to the shaft segment, the distal end segment including a distal end segment uptake lumen and a distal end segment return lumen, where the distal end segment central axis forms a non-zero angle with the shaft segment central axis when the catheter is in its unstressed configuration. In a second embodiment, the catheter includes: a shaft segment; and a distal end segment coupled to the shaft segment; where the uptake lumen distal end is terminated by a closed surface, further where the uptake lumen distal segment includes only one side hole. In a third embodiment, the catheter includes: an uptake lumen; and a return lumen; where at least a portion of the return lumen distal segment is helically coiled around the uptake lumen distal end.

28 Claims, 4 Drawing Sheets

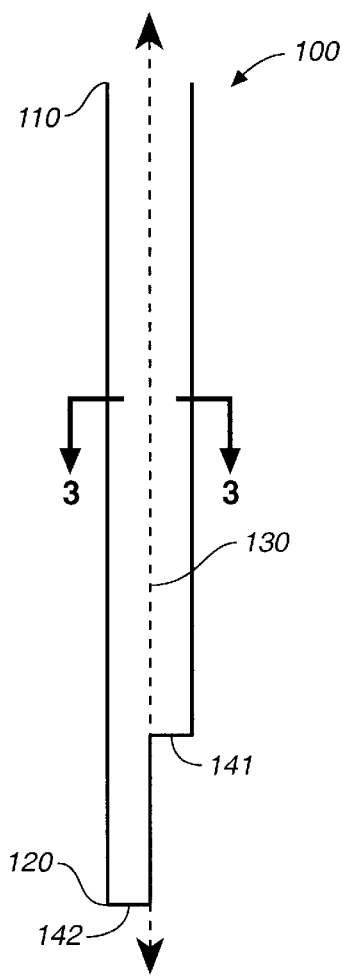
FIG._1
(PRIOR ART)
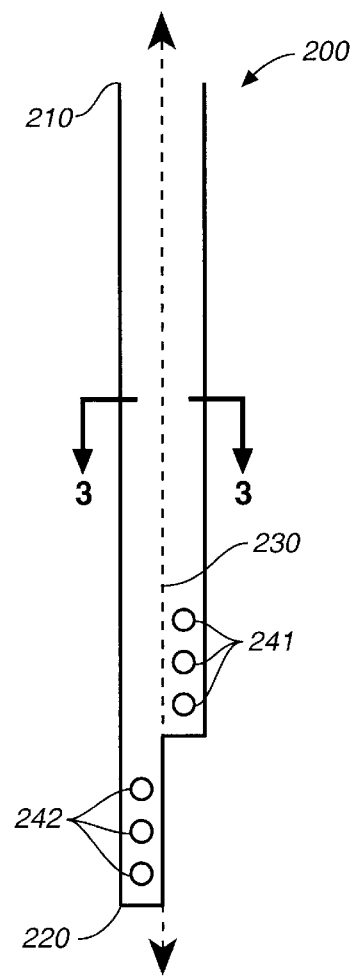
FIG._2
(PRIOR ART)
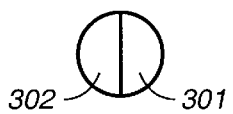 FIG._3a (PRIOR ART)
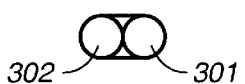 FIG._3b (PRIOR ART)
 FIG._3c (PRIOR ART)

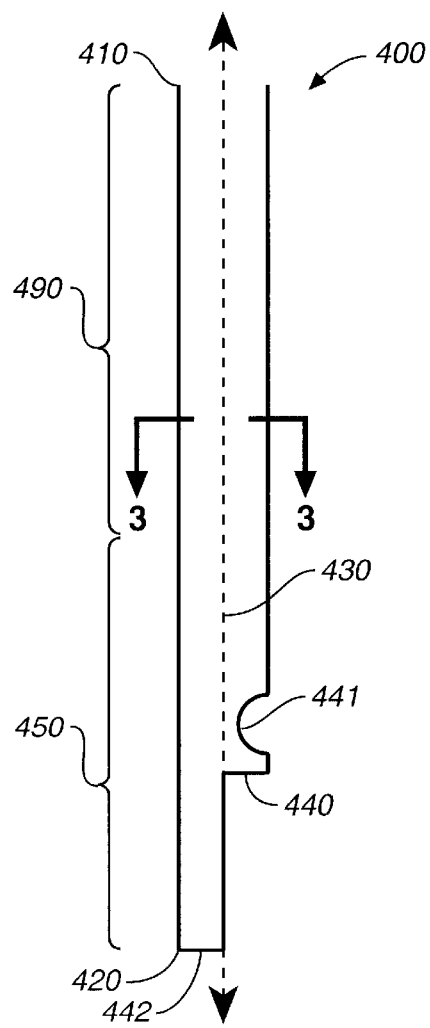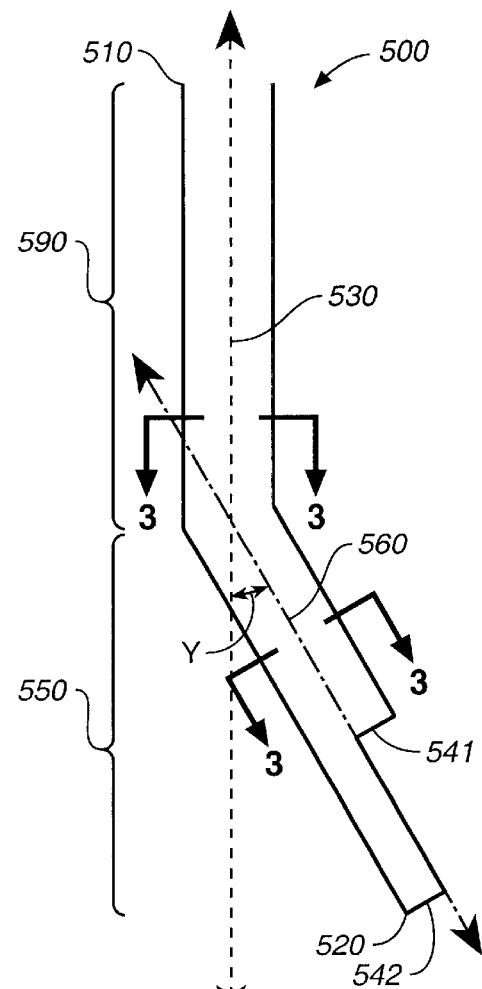
FIG._4        FIG._5

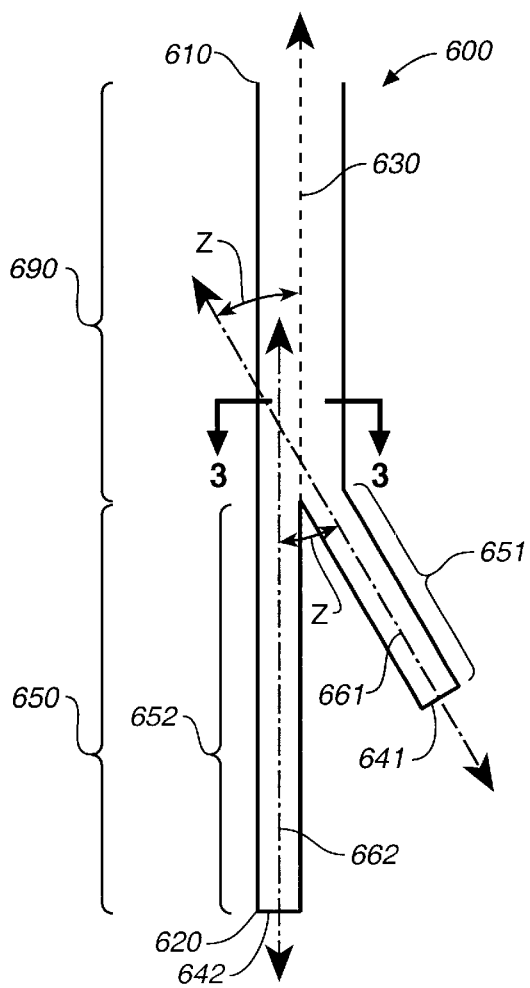
FIG._6
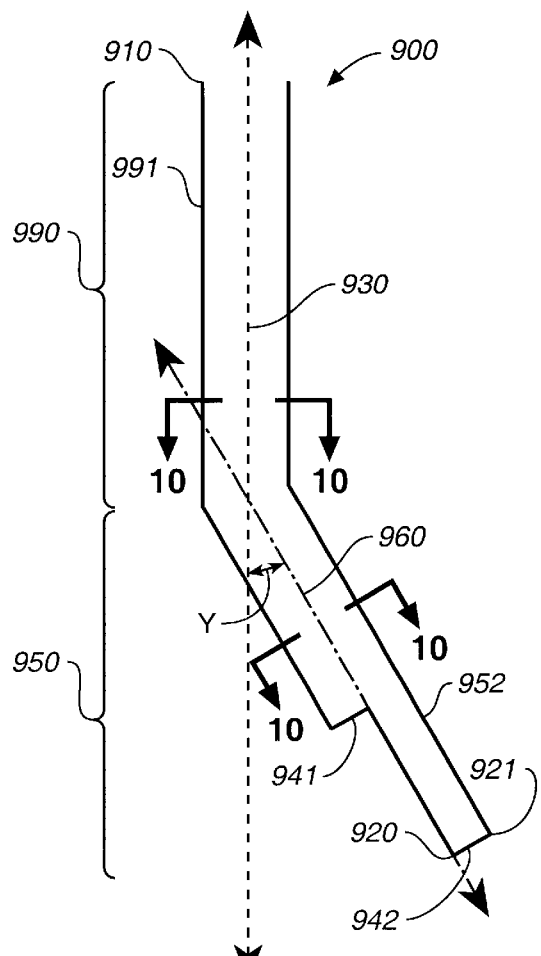
FIG._9
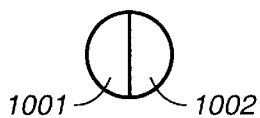
FIG._10a
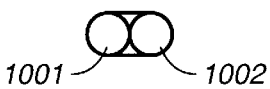
FIG._10b
FIG._10c

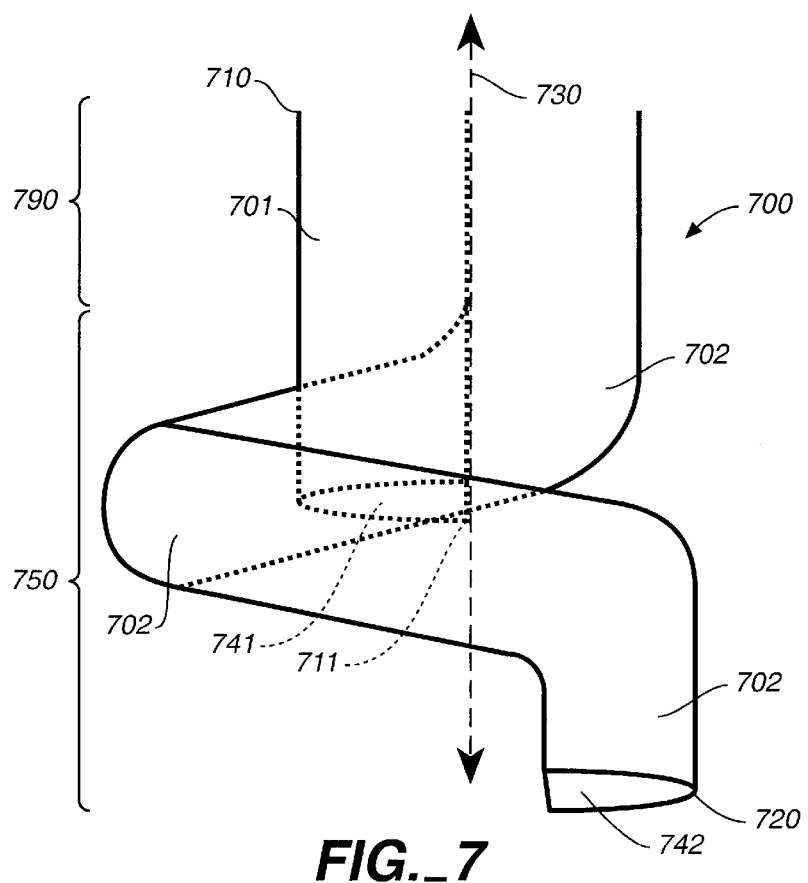
FIG._7
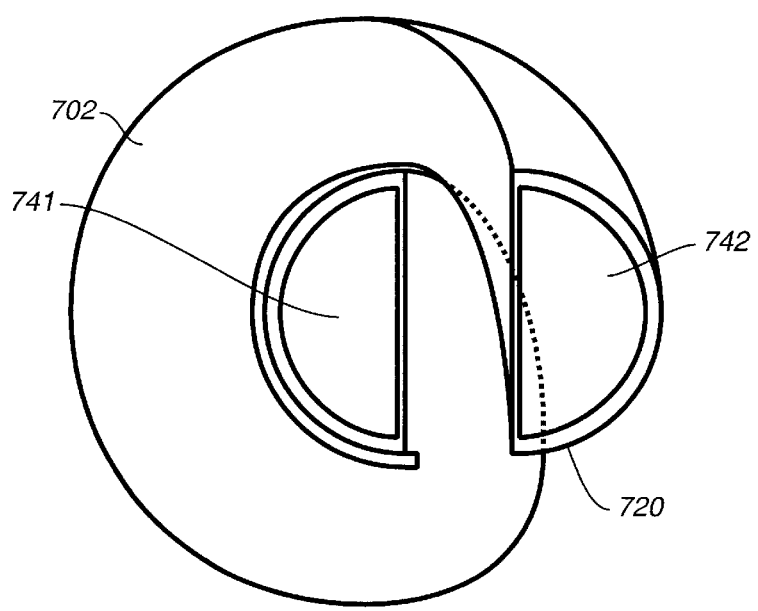
FIG._8

DOUBLE-LUMEN CATHETER

CROSS-REFERENCE TO RELATED APPLICATIONS

This application claims the benefit of U.S. Provisional Application Serial No. 60/210,294, filed Jun. 8, 2000, and entitled "Double-Lumen Catheters Used For Hemodialysis".

FIELD OF THE INVENTION

The present invention relates generally to catheters and, in particular, though not exclusively, to double-lumen catheters used for hemodialysis.

BACKGROUND OF THE INVENTION

Hemodialysis catheters are conventionally large double-lumen catheters. Generally, the lumens must be large enough to support flow rates greater than 250 c c/min through each lumen. A hemodialysis catheter resides within a large vein within the body or within the right atrium of the heart. The end of the catheter placed into a patient's body is referred to as the distal end of the catheter, while the end connected to a dialysis machine is called the proximal end. Blood is withdrawn out of a vein via an uptake lumen of the catheter and into the dialysis machine. The uptake lumen is also referred to herein as the withdrawal lumen. The dialyzed blood is returned to the body via the return lumen. The uptake lumen has an uptake lumen hole (also referred to as an uptake lumen opening) for withdrawal of blood from the body. The uptake lumen hole is typically disposed at the distal end of the uptake lumen. Similarly, the return lumen has a return lumen hole for return of blood to the body. The return lumen hole is typically disposed at the distal end of the return lumen. The uptake and return lumen holes are generally spatially separated from each other, typically with the uptake lumen hole located proximal to the return lumen. This is usually accomplished by making the uptake lumen shorter than the return lumen. The above configuration of the uptake and return lumen holes minimizes the immediate redialysis of blood just returned to the body.

FIG. 1 is a side view of a first embodiment of double lumen catheters in the prior art. In FIG. 1, catheter 100 includes a proximal end 110, a distal end 120, and a central axis 130. The central axis may also herein be referred to as the longitudinal axis. Catheter 100 also includes an uptake lumen end hole 141 and a return lumen end hole 142. As can be seen in FIG. 1, uptake lumen end hole 141 is located proximally with respect to return lumen end hole 142.

On occasion, prior art catheters, such as that shown in FIG. 1, fail to perform their intended function. The failure modes of these catheters are numerous. One common type of failure is occlusion of the uptake lumen end hole by the adjacent wall of the vein or by the wall of the right atrium. That is, when blood is withdrawn at a rapid rate from the vein via the uptake lumen, the uptake lumen end hole has a propensity to aspirate (or "suck up") against any adjacent structure. This adverse action of the uptake lumen end hole either limits the flow rate of the catheter or occludes blood flow entirely through the catheter.

Some of the available hemodialysis catheters address this problem by designing the uptake lumen to have several side holes. FIG. 2 is a side view of a prior art catheter having such side holes. Catheter 200, in FIG. 2, has a proximal end 210, a distal end 220, and a central axis 230. Catheter 200 also includes uptake lumen side holes 241 in the uptake lumen and return lumen side holes 242 in the return lumen. With this configuration, even if one side hole of the uptake lumen is sucked or aspirated against an adjacent wall, the catheter functions because the other side holes of the uptake lumen are not aspirated against the wall.

However, this design, in which multiple side holes are present to prevent occlusion by adjacent walls, presents a drawback of its own. When any hemodialysis catheter is not in use, both lumens are filled (or "locked") with an anticoagulant solution, typically concentrated heparin sulfate. This solution is intended to prevent blood clots from forming on or within the catheter's lumens. Such blood clots would occlude the lumens, leading to catheter failure. If the uptake lumen has multiple side holes, the anticoagulant solution leaks away at the catheter tip through these multiple side holes, causing an increased risk of blood clot formation on the catheter's tip, thus causing subsequent catheter failure.

A hemodialysis catheter whose uptake lumen consists of a single end hole will retain the anticoagulant solution. However, as detailed above, such a prior-art hemodialysis catheter retains a tendency to have its uptake lumen end hole aspirate against an adjacent wall and occlude the uptake lumen.

The intravenous portion of conventional hemodialysis catheters are linear in configuration. The lumens of such catheters run parallel to each other within a single, flexible silicone housing, with the lumens separated by a silicone septum. FIGS. 3a, 3b, and 3c are a first, second, and third embodiments, respectively, of the cross sectional view along each of lines 3—3 in FIGS. 1 and 2. The views in FIGS. 3a, 3b, and 3c represent different embodiments for partitioning the uptake and return lumens. In FIGS. 3a, 3b, and 3c, cross sections 301 and 302 represent cross sections of the uptake lumen and return lumen, respectively, in the three different embodiments of the cross sections of the catheter. FIGS. 3a, 3b, and 3c also represent three different embodiments of the view along the central axis from the distal end to the proximal end (as well as the view along the central axis from the proximal end to the distal end) in the catheters of FIGS. 1 and 2.

Discussion of prior art catheters, such as those described above, can be found in U.S. Pat. No. 5,209,723, U.S. Pat. No. 5,947,953, and U.S. Pat. No. 6,001,079, which are incorporated by reference herein.

Accordingly, there is a need for a catheter that addresses the above disadvantages of prior art catheters.

SUMMARY OF THE INVENTION

The present invention encompasses a catheter. In one embodiment, the catheter includes: a shaft segment, the shaft segment including a proximal end of the catheter and a shaft segment central axis, the shaft segment further including a shaft S segment uptake lumen and a shaft segment return lumen; a distal end segment coupled to the shaft segment, the distal end segment including a distal end of the catheter and a distal end segment central axis, the distal end segment further including a distal end segment uptake lumen and a distal end segment return lumen, where the distal end segment uptake and return lumens are coupled to the shaft segment uptake and return lumens, respectively; where the distal end segment central axis forms a non-zero angle with the shaft segment central axis when the catheter is in its unstressed configuration.

In a second embodiment, the catheter includes: a shaft segment, the shaft segment including a proximal end of the catheter and a shaft segment central axis; a distal end segment coupled to the shaft segment, the distal end segment including a distal end of the catheter and a distal end segment central axis; where the distal end segment central axis is parallel to the shaft segment central axis when the catheter is in its unstressed configuration, further where the distal end segment includes a return lumen and an uptake lumen having a return lumen distal end and an uptake lumen distal end, respectively, further where the uptake lumen distal end is terminated by a closed surface, further where the uptake lumen distal segment includes only one side hole.

In a third embodiment, the catheter includes: an uptake lumen including an uptake lumen shaft segment and an uptake lumen distal segment with an uptake lumen distal end; a return lumen including a return lumen shaft segment and a return lumen distal segment with a return lumen distal end; where the uptake lumen shaft segment is substantially parallel to the return lumen shaft segment, further where at least a portion of the return lumen distal segment is helically coiled around the uptake lumen distal end.

BRIEF DESCRIPTION OF THE DRAWINGS

FIG. 1 is a side view of a first embodiment of double-lumen catheter in the prior art.

FIG. 2 is a side view of a second embodiment of double-lumen catheter in the prior art.

FIGS. 3a, 3b, and 3c are three different embodiments of the cross sectional view along each of lines 3—3 in FIGS. 1, 2, 4, 5, and 6.

FIG. 4 is a side view of a first embodiment of the catheter of the present invention.

FIG. 5 is a side view of a second embodiment of the catheter of the present invention.

FIG. 6 is a side view of a third embodiment of the catheter of the present invention.

FIG. 7 is a side view of a fourth embodiment of the catheter of the present invention.

FIG. 8 is a bottom view from the distal end to the proximal end of the catheter in FIG. 7.

FIG. 9 is a side view of a fifth embodiment of the catheter of the present invention.

FIGS. 10a, 10b, and 10c are three embodiments of the cross sectional view along each of lines 10—10 in FIG. 9.

DETAILED DESCRIPTION

FIG. 4 is a side view of a first embodiment of the catheter of the present invention. Catheter 400, in FIG. 4, has a proximal end 410, a distal end 420, and a central axis 430. Catheter 400 includes a shaft segment 490 (which may also herein be referred to as the intravenous portion) and a distal end segment 450. In one embodiment, distal end segment is 450 is much smaller than the shaft segment 490. (Please note that figures in this application are not drawn to size.) Central axis 430 is a straight line that runs along the length of the catheter 400, including the shaft segment 490 and distal end segment 450.

Catheter 400 includes an uptake lumen side hole 441 and a return lumen end hole 442 in the distal end segment 450. In catheter 400, uptake lumen side hole 441 is the only uptake lumen hole. Catheter 400 does not have any other uptake lumen side holes in addition to uptake lumen side hole 441. Additionally, catheter 400 does not include an uptake lumen end hole since the distal end of uptake lumen 440 is sealed i.e., the uptake lumen distal end is terminated by a closed surface. In other words, unlike catheter 100 (in FIG. 1), catheter 400 does not include an uptake lumen end hole. Catheter 400 can be inserted by a physician into a vein or the atrium of a patient such that the uptake lumen side hole 441 is oriented in a direction opposite that of the nearest wall to help prevent adherence of the lumen to a vein or atrium wall. Thus, uptake lumen side hole 441 is a directable uptake lumen hole, i.e., it can be directed away from a vessel or atrium wall. This addresses the problem associated with prior art catheters, such as that shown in FIG. 1, which do not include a directable uptake lumen hole.

In one embodiment, the uptake lumen side hole 441 is directed away from a lateral wall of a vessel when the catheter is in the vessel. In one embodiment, the uptake lumen side hole 441 is medially oriented with respect to the lateral wall of the vessel.

Furthermore, since catheter 400 has only one uptake lumen hole, where the only uptake lumen hole is an uptake lumen side hole, it also addresses the problems associated with prior art catheters, such as that shown in FIG. 2, which include a plurality of uptake lumen side holes. As noted above, these prior art catheters allow leakage of anticoagulant solutions which may result in catheter failures.

Accordingly, catheter 400 of the present invention addresses the disadvantages of the catheters 100 and 200 of the prior art. In other words, catheter 400 minimizes obstruction of uptake lumen caused by either adherence of the catheter to the side walls of a vein or atrium or by a rapid diffusion of anticoagulant solutions from the catheter when the catheter is not in use.

FIG. 5 is a side view of a second embodiment of the catheter of the present invention. Catheter 500 has a proximal end 510, a distal end 520, and a central axis 530. Catheter 500 includes a shaft segment 590 and a distal end segment 550. Central axis 530 runs along the length of shaft segment 590. Distal end segment 550 includes central axis 560 which forms a non-zero angle Y with central axis 530. Thus, the distal end segment 550 is angled away from the central axis 530 of the catheter.

Angled distal end segment 550 includes both a portion of the uptake lumen and a portion of the return lumen. Three embodiments of the cross sectional view along line 3—3 in the distal end segment 550 are shown in FIGS. 3a, 3b, and 3c.

Angled distal end segment 550 includes a return lumen end hole 542 and an uptake lumen end hole 541 that is located proximally with respect to the return lumen end hole 542. Angled distal end segment 550 allows the uptake lumen end hole 541 of the uptake lumen of the catheter 500 to be directed away from the nearest vessel or atrium wall when the catheter is inserted into a patient. This helps prevent occlusion of the uptake lumen by the adjacent wall of the vein or right atrium. Furthermore, since catheter 500 includes only one uptake lumen hole it minimizes diffusion of anticoagulant solution from the catheter 500 when the catheter 500 is not in use.

In one embodiment, the uptake lumen end hole 541 is directed away from a lateral wall of a vessel when the catheter is in the vessel. In one embodiment, the uptake lumen end hole 541 is medially oriented with respect to the lateral wall of the vessel.

FIG. 6 is a side view of a third embodiment of the catheter of the present invention. In FIG. 6, catheter 600 has a proximal end 610, a distal end 620, and a central axis 630. Catheter 600 includes a shaft segment 690 and a distal end segment 650. Central axis 630 runs along the length of shaft segment 690.

Distal end segment 650 includes an uptake lumen end segment 651 and a return lumen end segment 652. Uptake lumen end segment 651 and return lumen end segment 652 each comprise separate tubes. Uptake lumen end segment 651 has a central axis 661 that forms a non-zero angle Z with central axis 630. Thus, uptake lumen end segment 651 is angled with respect to the central axis 630. On the other hand, return lumen end segment 652 has a central axis 662 that is parallel to the central axis 630. Thus, return lumen end segment 652 is not angled with respect to the central axis 630. However, there is a non-zero angle Z between central axis 662 of the return lumen end segment 652 and central axis 661 of the uptake lumen end segment 651. Thus, the return lumen end segment 652 is angled at an angle Z with respect to the uptake lumen end segment 651.

In catheter 600, the angle between central axis 661 and central axis 630 is the same as the angle between central axis 661 and central axis 662. In another embodiment, these angles may be different from each other. This may happen, for example, when there is a first non-zero angle A1 between central axis 662 and central axis 630 and a second non-zero angle A2 between central axis 661 and central axis 630, where A1 is not equal to A2.

Uptake lumen (and more specifically the uptake lumen end segment 651) includes an uptake lumen end hole 641. Similarly, return lumen (and more specifically the return lumen end segment 652) includes a return lumen end hole 642.

The angled uptake lumen end hole 641 can be directed away from the nearest vessel or atrium wall when the catheter is inserted into a patient. This reduces occlusion of the uptake lumen end hole 641 by the adjacent wall of the vein or right atrium as in the embodiment shown in FIG. 5. Furthermore, since catheter 600 includes only one uptake lumen hole it minimizes leakage of anticoagulant solution from the catheter 600 when the catheter 600 is not in use.

In one embodiment, the uptake lumen end hole 641 is directed away from a lateral wall of a vessel when the catheter is in the vessel. In one embodiment, the uptake lumen end hole 641 is medially oriented with respect to the lateral wall of the vessel.

FIGS. 3a, 3b, and 3c are three embodiments of the cross sectional view along each of lines 3—3 in FIGS. 4, 5, and 6. The views in FIGS. 3a, 3b, and 3c represent different embodiments for partitioning the uptake and return lumens in FIGS. 4, 5, and 6.

FIGS. 3a, 3b, and 3c also represent a bottom view from distal end 420 to the proximal end 410 along central axis 430. It is to be noted that in the case of such a bottom view, area 301 in FIGS. 3a, 3b, and 3c would represent the sealed end of the uptake lumen of catheter 400. FIGS. 3a, 3b, and 3c also represent a bottom view from distal end 520 to line 3—3 in distal end segment 550 along central axis 560 in FIG. 5.

Referring to FIG. 6, as noted above, uptake lumen end segment 651 and return lumen end segment 652 are each separate tubes. Thus, the bottom views from uptake lumen end hole 641 and return lumen end hole 642 along central axis 661 and central axis 662, respectively, would simply show the outline of the uptake lumen end hole 641 and the return lumen end hole 642, respectively. The outline can be a circle, an ellipse or any other configuration that may be used for a catheter lumen tube.

FIG. 7 is a side view of a fourth embodiment of the catheter of the present invention. Catheter 700, in FIG. 7, has a proximal end 710, a distal end 720, and a central axis 730. Catheter 700 includes an uptake lumen 701 and a return lumen 702. Catheter 700 includes a shaft segment 790 and a distal end segment 750. (As noted above, the drawings are not drawn to size. For example, even though the distal end segment 750 is shown as being longer than the shaft segment 790, in an actual embodiment, the distal end segment 750 is in fact much shorter than shaft segment 790.) Shaft segment 790 includes part of the uptake lumen 701 and part of the return lumen 702 disposed in a parallel position to the uptake lumen 701. Similarly, distal end segment 750 includes part of the uptake lumen 701 and part of the return lumen 702. In the distal end segment 750, the return lumen 702 is helically coiled around the uptake lumen 701. More specifically, the return lumen 702 is helically coiled around the uptake lumen distal end 711 and uptake lumen end hole 741. In one embodiment, the return lumen 702 helically coils 360 degrees about the uptake lumen 701 and the uptake lumen end hole 741, thus reducing occlusion of the uptake lumen end hole 741 by the adjacent wall of the vein or right atrium. Moreover, the portion of return lumen 702 helically coiled around the uptake lumen 701 serves a "bumper" which prevents inadvertent contact between the uptake lumen end hole 741 and a vessel or atrium wall. Thus, it shields the uptake lumen end hole 741 from the vessel or atrium wall.

The distal end of the return lumen 702 corresponds to the distal end 720 of catheter 700. At the distal end 720, the return lumen 702 includes a return lumen end hole 742. As can be seen in FIG. 7, the return lumen end hole 742 is disposed distally in relation to the uptake lumen end hole 741.

FIG. 8 shows a bottom view from the distal end 720 to the proximal end 710 along central axis 730. It shows uptake lumen end hole 741 and return lumen end hole 742. Additionally it shows return lumen 702 helically coiled around uptake lumen end hole 741.

In FIGS. 7 and 8, dashed lines (with the exception of central axis 730 which is intended to show an imaginary line in the catheter) represent contours of the catheter 700 that are hidden from view in the views represented by FIGS. 7 and 8. In FIG. 7, the view at the uptake lumen distal end 711 and the distal end 720 is slightly oblique so as to provide a view of end holes 741 and 742.

FIG. 9 is a side view of a fifth embodiment of the catheter of the present invention. Catheter 900 has a proximal end 910, a distal end 920, and a central axis 930. Catheter 900 includes a shaft segment 990 and a distal end segment 950. Central axis 930 runs along the length of shaft segment 990. Distal end segment 950 includes central axis 960 which forms a non-zero angle Y with central axis 930. Thus, the distal end segment 950 is angled away from the central axis 930 of the catheter.

Angled distal end segment 950 includes both a portion of the uptake lumen and a portion of the return lumen. Three embodiments of the cross sectional view along line 10—10 in the distal end segment 950 are shown in FIGS. 10a, 10b, and 10c, which are described in more detail below. Angled distal end segment 950 includes a return lumen end hole 942 and an uptake lumen end hole 941 that is located proximally with respect to the return lumen end hole 942. Angled distal end segment 950 allows the uptake lumen end hole 941 of the uptake lumen of the catheter 900 to be directed away from the nearest vessel or atrium wall when the catheter is inserted into a patient. This reduces occlusion of the uptake lumen by the adjacent wall of the vein or right atrium. Furthermore, since catheter 900 includes only one uptake lumen hole it minimizes leakage of anticoagulant solution from the catheter 900 when the catheter 900 is not in use.

An additional factor that helps reduce occlusion of the uptake lumen in catheter 900 is the relative position of the uptake lumen, more specifically uptake lumen end hole 941, within catheter 900. As can be seen in FIG. 9, uptake lumen end hole 941 is located between the lateral side wall 991 of the shaft 990 and the medial tip 921 of the distal end 920. In this configuration, uptake lumen end hole 941 is directed away from the lateral wall of a vessel due to the fact that the distal end segment 950 is angled away from the lateral wall. In one embodiment, the uptake lumen end hole 941 is medially oriented with respect to the lateral wall of the vessel. The lateral side wall 991 of the shaft would help maintain a separation between the lateral wall of the vessel and the uptake lumen end hole 941. Similarly, return lumen end segment 952 of distal end segment 950 would help maintain a separation between the medial wall of the vessel and the uptake lumen end hole 941. Additionally, the return lumen end segment 952 shields the uptake lumen end hole 941 from the medial wall of the vessel.

FIGS. 10*a*, 10*b*, and 10*c* are three embodiments of the cross sectional view along each of lines 10—10 in FIG. 9. FIGS. 10*a*, 10*b*, and 10*c* also represent a bottom view from the bottom of the shaft segment 990 to the proximal end 910 along central axis 930. FIGS. 10*a*, 10*b*, and 10*c* also represent a bottom view from distal end 920 to line 10—10 in the distal end segment 950 along central axis 960. The views in FIGS. 10*a*, 10*b*, and 10*c* represent different embodiments for partitioning the uptake and return lumens in FIG. 9. In FIGS. 10*a*, 10*b*, and 10*c*, area 1001 represents a cross section of the uptake lumen in catheter 900 while area 1002 represents a cross section of the return lumen in catheter 900.

Double lumen catheters such as 400, 500, 600, 700, and 900 can be made of flexible plastic material such as silicone, but need not be made of silicone. Catheters 400, 500, 600, 700 and 900 in FIGS. 4–9 are shown in their unstressed configurations, i.e., their rest positions, but can be stretched or deformed into relatively linear configurations for the purpose of introduction into the body. Thus, in the rest position, each of catheters 500, 600, and 900 includes a distal end segment that is angled with respect to the central axis of the catheter shaft segment. Similarly, in the rest position, catheter 700 has a helically coiled segment surrounding the uptake lumen end hole.

In the above embodiments, the angle Y may, for example, be in the range of 5 to 60 degrees, 5 to 45 degrees, or 5 to 30 degrees. Similarly, the angle Z may, for example, be in the range of 5 to 60 degrees, 5 to 45 degrees, or 5 to 30 degrees. As noted above, catheters 400, 500, 600, 700 and 900 in FIGS. 4–9 are shown in their rest positions. Accordingly, the above ranges are examples of ranges for angles Y and Z when the catheters are in their rest positions.

In the above description one lumen in each of the drawings has been referred to as an uptake lumen while the other lumen has been referred to as the return lumen. It is to be noted that the present invention may encompass embodiments in which the designation of uptake lumen and return lumen are the reverse of those in the above description.

While the present invention has been particularly described with respect to the illustrated embodiments, it will be appreciated that various alterations, modifications and adaptations may be made based on the present disclosure, and are intended to be within the scope of the present invention. While the invention has been described in connection with what are presently considered to be the most practical and preferred embodiments, it is to be understood that the present invention is not limited to the disclosed embodiment but, on the contrary, is intended to cover various modifications and equivalent arrangements included within the scope of the appended claims.

What is claimed is:

1. A catheter comprising:

a shaft segment, said shaft segment including a proximal end of the catheter and a shaft segment central axis, wherein said shaft segment comprises a shaft segment uptake lumen and a shaft segment return lumen;

a distal end segment coupled to the shaft segment, said distal end segment including a distal end of the catheter and a distal end segment central axis, wherein said distal end segment comprises a distal end segment uptake lumen and a distal end segment return lumen, further wherein said distal end segment uptake and return lumens are coupled to said shaft segment uptake and return lumens, respectively;

wherein said distal end segment central axis forms a non-zero angle with the shaft segment central axis when said catheter is in its unstressed configuration.

2. The catheter of claim 1, wherein the non-zero angle is in the range of 5 to 60 degrees.

3. The catheter of claim 1, wherein the non-zero angle is in the range of 5 to 45 degrees.

4. The catheter of claim 1, wherein the non-zero angle is in the range of 5 to 30 degrees.

5. The catheter of claim 1, wherein said distal end segment uptake lumen and distal end segment return lumen comprise a distal end segment uptake lumen central axis and distal end segment return lumen central axis, respectively.

6. The catheter of claim 5, wherein the distal end segment uptake lumen central axis and distal end segment return lumen central axis are parallel to the distal end segment central axis.

7. The catheter of claim 5, wherein the distal end segment uptake lumen central axis is parallel to the distal end segment central axis, further wherein the distal end segment return lumen central axis is parallel to the shaft segment central axis.

8. The catheter of claim 5, wherein the distal end segment uptake lumen central axis is parallel to the distal end segment central axis, further wherein the distal end segment return lumen central axis forms a second non-zero angle with the shaft segment central axis.

9. The catheter of claim 1, wherein said distal end segment uptake lumen comprises an uptake hole and said distal end segment return lumen comprises a return hole.

10. The catheter of claim 9, wherein said uptake hole is located proximally with respect to the return hole.

11. The catheter of claim 9, wherein said uptake hole is directed away from a lateral wall of a vessel when the catheter is in the vessel.

12. The catheter of claim 9, wherein said shaft segment comprises a lateral side wall, further wherein said uptake hole is directed away from the lateral side wall such that a separation is maintained between a lateral wall of a vessel and said uptake hole when the catheter is in the vessel and the lateral side wall abuts the lateral wall of the vessel.

13. The catheter of claim 9, wherein said distal end segment return lumen comprises a return lumen end segment, further wherein said return lumen end segment maintains a separation between a medial wall of a vessel and said uptake hole when the catheter is in the vessel.

14. The catheter of claim 9, wherein said distal end segment return lumen comprises a return lumen end segment, further wherein said return lumen end segment shields the uptake hole from a medial wall of a vessel when the catheter is in the vessel.

15. The catheter of claim 11, wherein said uptake hole is medially oriented with respect to the lateral wall of the vessel.

16. The catheter of claim 1, wherein the catheter is comprised of a flexible plastic material.

17. A catheter comprising:
   a shaft segment, said shaft segment including a proximal end of the catheter and a shaft segment central axis;
   a distal end segment coupled to the shaft segment, said distal end segment including a distal end of the catheter and a distal end segment central axis;
   wherein said distal end segment central axis is parallel to the shaft segment central axis when said catheter is in its unstressed configuration, further wherein said distal end segment comprises a return lumen and an uptake lumen having a return lumen distal end and an uptake lumen distal end, respectively, further wherein the uptake lumen distal end is terminated by a closed surface, further wherein the uptake lumen distal segment includes only one side hole.

18. The catheter of claim 17, wherein said shaft segment comprises a shaft segment uptake lumen and a shaft segment return lumen, further wherein said shaft segment uptake and return lumens are coupled to the distal end segment uptake and return lumens, respectively.

19. The catheter of claim 17, wherein said distal end segment return lumen comprises a return hole, further wherein said only one side hole is located proximally with respect to the return hole.

20. The catheter of claim 17, wherein said one side hole is directed away from a lateral wall of a vessel when the catheter is in the vessel.

21. The catheter of claim 20, wherein said one side hole is medially oriented with respect to the lateral wall of the vessel.

22. The catheter of claim 17, wherein the catheter is comprised of a flexible plastic material.

23. A catheter comprising:
   an uptake lumen including an uptake lumen shaft segment and an uptake lumen distal segment with an uptake lumen distal end;
   a return lumen including a return lumen shaft segment and a return lumen distal segment with a return lumen distal end;
   wherein the uptake lumen shaft segment is substantially parallel to the return lumen shaft segment, further wherein at least a portion of the return lumen distal segment is helically coiled around the uptake lumen distal end.

24. The catheter of claim 23, wherein said uptake lumen distal end segment comprises an uptake hole and said return lumen distal end segment comprises a return hole, further wherein said return hole is located distally with respect to the uptake hole.

25. The catheter of claim 23, wherein the return lumen end segment comprises a portion parallel to the uptake lumen end segment and disposed more distally than the uptake lumen distal end.

26. The catheter of claim 23, wherein said uptake lumen distal segment includes an uptake lumen end hole at the uptake lumen distal end, further wherein said portion of the return lumen distal segment helically coils 360 degrees about the uptake lumen end hole.

27. The catheter of claim 26, wherein said portion of the return lumen distal segment shields the uptake lumen end hole from a blood vessel or atrium wall when said catheter is disposed in a blood vessel or atrium.

28. The catheter of claim 23, wherein the catheter is comprised of a flexible plastic material.

* * * * *